United States Patent
Doyle et al.

(10) Patent No.: US 7,575,744 B2
(45) Date of Patent: Aug. 18, 2009

(54) COMPOSITION AND METHOD FOR INHIBITION OF MICROORGANISMS

(75) Inventors: Michael P. Doyle, Peachtree City, GA (US); Tong Zhao, Peachtree City, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 330 days.

(21) Appl. No.: 10/535,357

(22) PCT Filed: Nov. 24, 2003

(86) PCT No.: PCT/US03/37526

§ 371 (c)(1),
(2), (4) Date: May 18, 2005

(87) PCT Pub. No.: WO2004/048597

PCT Pub. Date: Jun. 10, 2004

(65) Prior Publication Data

US 2006/0073129 A1   Apr. 6, 2006

Related U.S. Application Data

(60) Provisional application No. 60/428,863, filed on Nov. 25, 2002.

(51) Int. Cl.
*A01N 63/00* (2006.01)
*C12N 1/20* (2006.01)
*C12P 1/00* (2006.01)
*D06M 16/00* (2006.01)

(52) U.S. Cl. .................. 424/93.4; 435/252.1; 435/264; 435/267; 435/821; 435/822

(58) Field of Classification Search ........................ None
See application file for complete search history.

(56) References Cited

U.S. PATENT DOCUMENTS

| 5,186,962 | A |   | 2/1993 | Hutkins et al. |
| 5,308,615 | A | * | 5/1994 | DeLoach et al. ........... 424/93.3 |
| 5,451,369 | A | * | 9/1995 | Daeschel et al. .............. 422/28 |
| 5,869,066 | A |   | 2/1999 | Pace et al. |
| 6,080,401 | A |   | 6/2000 | Reddy et al. |

FOREIGN PATENT DOCUMENTS

WO   WO 02/056694   7/2002

OTHER PUBLICATIONS

PCT International Search Report for PCT/US2003/037526 completed by the U.S. Searching Authority on May 26, 2004.
Leriche et al., "Behavior of *L. monocytogenes* in an artificially made biofilm of a nisin-producing strain of *Lactococcus lactis*", *International Journal of Food Microbiology*, 51(2): 169-182 (1999).
Jeong et al., "Growth of *Listeria monocytogenes* at 21° C. in biofilms with microorganisms islolated from meat and dairy processing environments", *Lebensmittel-Wissenschaft and Technologie*, 27(5): 415-424 (1994).
Lasagno et al., "Selection of bacteriocin producer strains of lactic acid bacteria from a dairy environment", The *New Microbiologica: Official Journal of the Italian Society for Medical, Odontoiatric, and Clinical Microbiology*, 25(1) 37-44 (2002).
Sulzer et al., "Growth inhibition of *Listeria* spp. on Camembert cheese by bacteria producing inhibitory substances", *International Journal of Food Microbiology*, 14(3): 287-296 (1991).
Jeong et al., "Growth of *Listeria monocytogenes* at 10° C. in biofilms with microorganisms isolated from meat and dairy processing environments", *Journal of Food Proctection*, 57(7): 576-586 (1994).

* cited by examiner

*Primary Examiner*—David M. Naff
*Assistant Examiner*—Deborah K. Ware
(74) *Attorney, Agent, or Firm*—Barnes & Thornburg LLP

(57) ABSTRACT

A composition and method for the inhibition of microorganisms.

7 Claims, 1 Drawing Sheet

COMPOSITION AND METHOD FOR INHIBITION OF MICROORGANISMS

CROSS REFERENCE TO RELATED APPLICATIONS

This application is a U.S. national counterpart application of international application serial No. PCT/US2003/037526 filed Nov. 24, 2003, which claims priority to U.S. Provisional Patent Application No. 60/428,863 filed Nov. 25, 2002. The entirety of which is hereby incorporated by reference.

FIELD OF THE INVENTION

The present invention relates generally to a composition and method for the inhibition of microorganisms, and more particularly to a composition and method for controlling *Listeria monocytogenes* in food processing facilities or on a food product by, for example, a probiotic microorganism, such as competitive exclusion microorganisms.

BACKGROUND OF THE INVENTION

The control of contamination by microorganisms is a recognized problem in the food processing industry. The process of preparing food products is largely concerned with preventing the contamination of such food products with harmful microorganisms. For example, in the meat packing industry, many types of microorganisms can cause food poisoning if contamination takes place. These microorganisms include *E. coli, Salmonella, Listeria monocytogenes, Staphylococcus aureus, Bacillus anthracis, Campylobacter coli, Campylobacter jejuni, Yersinia enterocolitica, Yersinia pseudotuberculosis, Brucella,* and *Clostridium*. One microorganism of particular concern for the food processing industry is *Listeria monocytogenes* (hereinafter referred to as *L. monocytogenes*) since studies indicate that certain strains of *L. monocytogenes* can become well established in a food-processing facility and remain members of the resident microbial flora for months or years. Moreover, investigations of several outbreaks of listeriosis revealed that environmental contamination of food processing facilities was the primary source of *L. monocytogenes* in many commercially prepared ready-to-eat (RTE) processed foods.

In general, *L. monocytogenes* has a widespread occurrence in nature and is capable of surviving and growing under a variety of conditions, including growing in soil and aqueous environments. For example, *L. monocytogenes* has been isolated from 8.4 to 44% of samples obtained from grain fields, pastures, mud, animal feces, wildlife feeding grounds, and related sources, and can survive in moist soils for more than 295 days. Furthermore, *L. monocytogenes* is a nonfastious organism that thrives in cool, damp environments. Moreover, this organism can grow at temperatures typically used to refrigerate processed foods which presents particular problems for the food processing industry.

As previously mentioned, *L. monocytogenes* thrives in cool, damp environments which is why high populations of this organism frequently occur in floor drains of food processing facilities. These *L. monocytogenes*-contaminated floor drains can serve as a point of contamination for the processing plant environment and food products. Decontaminating floor drains of listerae is especially challenging because the population of *L. monocytogenes* is typically enveloped in a biofilm, and the biofilm provides the microorganism with unusual protection against disinfectants and conventional treatments available to control pathogens on environmental surfaces. Therefore, although major improvements have been made in food processing plant layout, equipment design, and in procedures for cleaning and sanitizing food processing facilities, controlling the widely distributed psychrotrophic *L. monocytogenes* in food processing facilities remains a formidable challenge for the entire food industry as demonstrated by the fact that environmental testing results indicate that *L. monocytogenes* continues to be introduced into food processing environments. Accordingly, a composition and method for the inhibition of microorganisms such as *L. monocytogenes* is desirable.

SUMMARY OF THE INVENTION

According to one illustrative embodiment, there is provided a method of treating a surface of a food processing facility which has a first population of microorganisms disposed thereon. The method includes disposing (i) a biofilm containing a second population of microorganisms and/or (ii) a second population of microorganisms that forms a biofilm onto the surface of the food processing facility. The method also includes inhibiting the growth of the first population of microorganisms on the surface of the food processing facility with the second population of microorganisms.

According to another illustrative embodiment, there is provided a method of inhibiting the growth of *Listeria monocytogenes* on a surface of a food processing facility. The method includes inoculating the surface of the food processing facility with antimicrobial bacteria that can adhere to surfaces. The method also includes inhibiting the growth of the *Listeria monocytogenes* on the surface of the food processing facility with the bacteria adhering to the surface. For example, the bacteria can be contained in a biofilm so that it adheres to the surface or the bacteria can be one that forms a biofilm such that it adheres to the surface.

According to another illustrative embodiment, there is provided a method of inhibiting the growth of *Listeria monocytogenes* on a surface of a food processing facility. The method includes inoculating the surface of the food processing facility with a microorganism selected from the group consisting of bacteria from the genus *Enterococcus* and bacteria from the genus *Lactococcus*. The method also includes inhibiting the growth of the *Listeria monocytogenes* on the surface of the food processing facility with the bacteria.

According to still another illustrative embodiment, there is provided a method of inhibiting the growth of *Listeria monocytogenes* on a surface of a food processing facility. The method includes inoculating the surface of the food processing facility with antimicrobial bacteria that can adhere to surfaces such as antimicrobial bacteria contained in a biofilm, wherein the bacteria are selected from the group consisting of *Enterococcus durans, Lactococcus lactis,* and *Lactobacillus plantarum*. The method also includes inhibiting the growth of the *Listeria monocytogenes* on the surface of the food processing facility with the bacteria contained in the biofilm.

According to yet another illustrative embodiment, there is provided a kit for inhibiting the growth of a first microorganism population disposed on a surface. The kit can include a biofilm and a second microorganism population disposed in the biofilm. In the alternative, the kit can include a microorganism capable of forming a biofilm when disposed on a surface. In another alternative the kit can include a biofilm and a microorganism, where the microorganism is placed in the biofilm prior to being disposed on the surface. The second microorganism population is inhibitory to the first microorganism population when the second microorganism population is placed in the presence of the first microorganism population.

According to still another illustrative embodiment, there is provided an inoculant composition. The inoculant composition includes a biofilm having disposed therein at least one of the following: *Enterococcus durans* 141-1 having ATCC accession number PTA-4758, *Enterococcus durans* 152 having ATCC accession number PTA-4759, *Lactococcus lactis* C-1-92 having ATCC accession number PTA-4760, or *Lactococcus lactis* C-1-152 having ATCC accession number PTA-4761 or mixtures thereof. Each of said strains having been deposited with the American Type Culture Collection (ATCC; 10801 University Blvd., Manassas, Va. 20110-2209) on Oct. 15, 2002.

According to yet another illustrative embodiment, there is provided a biologically pure culture of bacteria selected from *Enterococcus durans* 141-1 having ATCC accession number PTA-4758, *Enterococcus durans* 152 having ATCC accession number PTA-4759, *Lactococcus lactis* C-1-92 having ATCC accession number PTA-4760, or *Lactococcus lactis* C-1-152 having ATCC accession number PTA-4761.

According to still another illustrative embodiment, there is provided a kit for inhibiting the growth of a first microorganism population disposed on a surface. The kit includes a biofilm and a second microorganism population for disposing in the biofilm. The second microorganism population is inhibitory to the first microorganism population when the second microorganism population is placed in the presence of the first microorganism population.

According to yet another illustrative embodiment, there is provided a method for selecting bacteria which inhibit the growth of *Listeria monocytogenes*. The method includes isolating naturally-occurring bacteria from a food processing facility. The method also includes culturing the isolated naturally-occurring bacteria. The method further includes testing the isolated naturally-occurring bacteria for the ability to inhibit the growth of *Listeria monocytogenes*.

According to still another illustrative embodiment, there is provided a method of selecting inhibitory bacteria. The method includes isolating naturally-occurring bacteria populations from a food processing facility. The method also includes culturing the isolated naturally-occurring bacteria populations. The method further includes testing each isolated naturally-occurring bacteria population for the ability to inhibit the growth of a microorganism, where isolated naturally-occurring bacteria populations having the ability to inhibit the growth of the microorganism are identified as a population of inhibitory bacteria.

According to still another illustrative embodiment, there is provided a culture of microorganisms that includes *Enterococcus durans* having ATCC accession number PTA-4758.

According to still another illustrative embodiment, there is provided a culture of microorganisms that includes *Enterococcus durans* having ATCC accession number PTA-4759.

According to still another illustrative embodiment, there is provided a culture of microorganisms that includes *Lactococcus lactis* having ATCC accession number PTA-4760.

According to still another illustrative embodiment, there is provided a culture of microorganisms that includes *Lactococcus lactis* having ATCC accession number PTA-4761.

According to still another illustrative embodiment, there is provided a method of treating a food product having a first population of microorganisms disposed thereon. The method includes (a) disposing a second population of microorganisms onto the surface of the food product and (b) inhibiting the growth of the first population of microorganisms on the food product with the second population of microorganisms. If desired, the second population of microorganisms can be capable of forming a biofilm.

DETAILED DESCRIPTION

Figure 1:
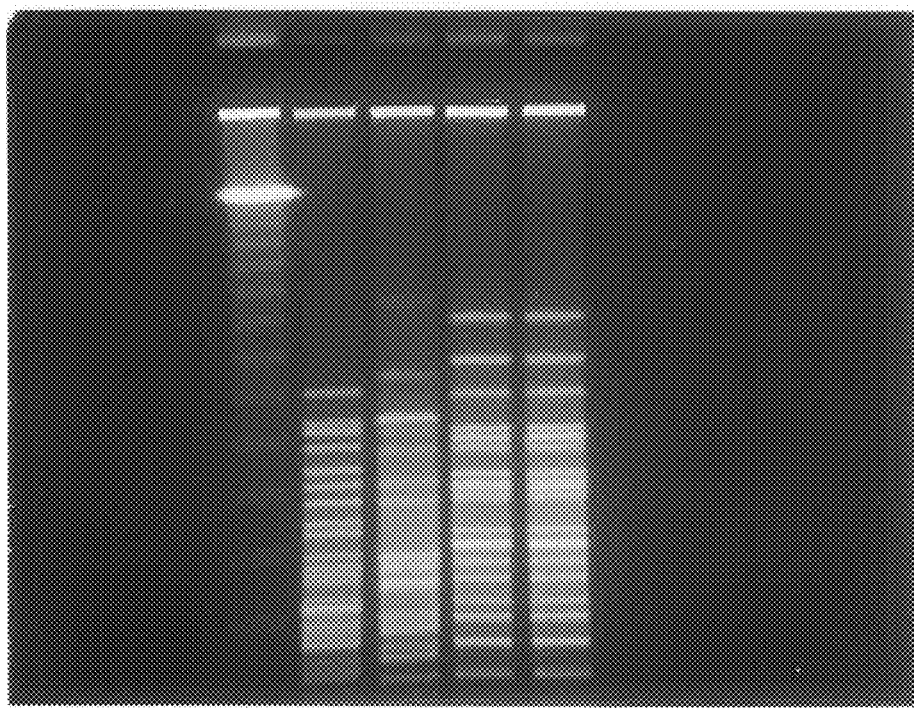
FIG. 1 illustrates the results of analyzing four probiotic isolates for their DNA fingerprinting by pulsed field-gel electrophoresis; lane 1 Lambda ladder DNA standard, lane 2 C-1-92 [*L. lactis* subsp. *lactis*], lane 3 C-1-152 [*L. lactis* subsp. *lactis*], lane 4 141-1 [*E. durans*], and lane 5 152 [*E. durans*].

While the invention is susceptible to various modifications and alternative forms, specific exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within in the spirit and scope of the invention.

Materials and Methods

Bacterial strains: A five-strain mixture of *L. monocytogenes*, including LM101 (serotype 4, salami isolate), LM112 (serotype 4, salami isolate), LM113 (serotype 4, pepperoni isolate), H9666 (serotype 1/2c, human isolate) and ATCC 5779 (serotype 1/2c, cheese isolate) from the UGA Center for Food Safety culture collection were used. Each strain was individually grown in tryptic soy broth with 0.6% yeast extract (TSBYE, Becton Dickinson, Sparks, Md.) at 37° C. for 16 h. The cultures were sedimented by centrifugation at 8,000×g for 20 min and resuspended in 0.1% peptone. The optical density of each strain was adjusted in a spectrophotometer with 0.1% peptone to an OD reading of 0.5 (ca. $10^8$ cfu/ml) at 630 nm. An equal volume of culture of each of the five strains was combined to obtain a 5-strain mixture of approximately equal cell numbers of each strain.

Isolation and Screening of Microorganisms for Metabolites Antagonistic to *L. monocytogenes*

Biofilm samples collected from floor drains at different food processing plants having a recent history of no detectable *L. monocytogenes* were used to obtain isolates of bacteria and yeasts. Two methods, which included a direct plating and an enrichment culture procedure, were used to isolate these microorganisms. Tryptic soy broth (TSB, 10 ml) was added to each biofilm sample (ca. 1 g) and biofilm preparations were serially diluted (1:10) in 0.1% peptone to $10^{-3}$. A volume of 0.1 ml of each dilution was plated on dichloran rose bengal chloramphenicol agar (DRBC) and tryptic soy agar (TSA) plates in duplicate, with DRBC plates incubated at 30° C. for 72 h and TSA plates incubated at 37° C. for 24 h. Biofilm preparation (1 ml) also was added to 9 ml of TSB and incubated at 37° C. for 24 h. Enrichment cultures were serially diluted in 0.1% peptone and 0.1-ml portions of dilutions of $10^{-5}$ to $10^{-8}$ were plated onto TSA and DRBC plates, and incubated according to the conditions described above. Ten colonies per biofilm specimen were selected randomly from plates and streaked for isolation.

Two methods, including the spot-on-lawn assay and the double layer assay, and two temperatures (37° C. and 15° C.) were used to screen isolates for anti-listerial activity. For the spot on-lawn-assay, 0.1 ml of ca. $10^7$ cells of the 5-strain mixture of *L. monocytogenes*/ml was plated onto each of duplicate TSA plates. Candidate competitive exclusion inhibition isolates were grown individually in TSB at 37° C. for 24 h, cells were sedimented by centrifugation (4,000×g for 20 min), and the supernatant fluid of each culture was filter-sterilized (0.22-μm-pore-size cellulose acetate membrane; Nalgene Co., Rochester, N.Y.). A 12-mm disc (Dispens-O-Disc; Difco Laboratories, Detroit, Mich.) was placed onto the surface of each TSA plate, and 0.1 ml of filter-sterilized supernatant fluid from a single culture was applied to the surface of the disc. The plates were incubated at 37° C. for 24 h and observed for zones of inhibition. In addition, a disc with nisin (3.125 µg; Sigma, St. Louis, Mo.) was used as the positive control and a disc with 0.1 M phosphate-buffered saline (PBS), pH 7.2, was used as the negative control.

The double-layer assay, also a two-step procedure, involved first growing a spot-inoculated candidate competitive inhibition isolate on TSA and then applying a second layer of growth medium containing the 5-strain mixture of *L. monocytogenes*. Specifically, an individual colony of competitive bacteria was inoculated in the center of each of two the TSA plates and incubated for 24 h at 37° C. A 5-strain mixture of *L. monocytogenes* was added at $10^6$ cfu/ml to brain heart infusion with 0.4% agar (BHIA, Difco) at 50° C. and mixed for 1 min at 200 rpm with a magnetic stir bar. The mixture (8 ml) was poured onto each TSA plate as a second layer and allowed to cool to room temperature. The cultures were incubated for 24 h at 37° C. and observed for zones of inhibition. Nisin-producing *Lactococcus lactis* subsp. *lactis* (ATCC 11454) was used as the positive control and a yeast isolate, which was obtained from this study and confirmed to have no inhibitory effect on the growth of *L. monocytogenes* was used as the negative control.

Competitive Inhibition in Broth Cultures at Different Temperatures

All isolates having anti-*L. monocytogenes* activity were further tested in TSBYE for competitive growth at temperatures ranging from about 4° C. to about 37° C., for example, 4° C., 8° C., 15° C. or 37° C. An individual isolate of a candidate competitive microorganism at ca. $10^7$ to $10^9$ (range $10^{6.7}$-$10^{9.0}$) cfu in 0.1 ml and 0.1 ml of ca. $10^5$ to $10^6$ (range $10^{5.2}$-$10^{6.6}$) cfu of a 5-strain mixture of *L. monocytogenes* were added to 10 ml of TSBYE and incubated at 4°, 8°, 15° or 37° C. Cultures (1 ml) were sampled at intervals of 0, 8 and 24 h for incubation at 37° C., at 0, 1, 2, 3, 7, 10 and 14 days for 15° C., at 0, 1, 7, 14 and 21 days for 8° C., and at 0, 2, 7, 14, 21 and 28 days for 4° C., and enumerated for *L. monocytogenes* on modified Oxford agar (MOX, Difco) at 37° C. for 48 h and for competitive microorganism count on TSA at 37° C. for 48 h.

Identification of Competitive Microorganisms

Bacterial isolates having antagonistic activity to *L. monocytogenes* at all four temperatures evaluated were assayed by Gram stain, biochemical assays (API CHB and API CHL; bioMérieux Industry, l'Etoile, France), and 16S rRNA gene alignment profile analysis (Midi Labs, Newark, Del.) for identification of genus and species. Preparation of stainless steel coupons: Stainless steel (T-304, Tull Metals Company, Atlanta, Ga.) coupons (4 cm×2.5 cm) were washed by a 10-min immersion with agitation (150 rpm) in 1000 ml of an aqueous 2% RBS 35 Detergent solution (20 ml of RBS 35 Concentrate per liter of tap water at 50° C.; Pierce, Rockford, Ill.), and rinsed by immersion in 1000 ml of tap water (initially at 50° C.) with agitation (150 rpm) for 25 min. Five additional 1-min immersions with agitation (150 rpm) in 1000 ml of distilled water at ambient temperature were performed. The coupons were dried and a hydrophobic marker was used to encircle an area of 1.13 cm in diameter. The coupons were then individually wrapped in aluminum foil and autoclaved at 121° C. for 30 min.

Competitive inhibition of *L. monocytogenes* in a biofilm: Biofilms were grown using a modification of the protocol described by Leriche and Carpentier, Viable but non-culturable *Salmonella typhimurium* in single- and binary-species biofilms in response to chlorine treatment. J. Food Prot. 58:1186-1191 (1995) which is incorporated herein by reference and Chae and Schraft, Cell viability of *Listeria monocytogenes* biofilms. Food Microbiol. 18:103-112 (2001) which is incorporated herein by reference. The protocol was modified to include increasing the circle to a diameter of 1.13 cm and adjusting the incubation temperatures and sampling times to produce examples of the biofilms described herein. A biofilm is defined as an assemblage, or organized group, of microbial cells, wherein the assemblage is irreversibly associated with a surface and enclosed in a matrix of primarily polysaccharide material. An inoculum of 0.1 ml of $10^{6.1}$-$10^{8.4}$ cfu of candidate competitive microorganisms and 0.1 ml of $10^{2.6}$-$10^{4.6}$ cfu of a 5-strain mixture of *L. monocytogenes* were deposited in a biofilm and placed within the marked area of the stainless steel coupon. The coupon was then placed in a humidity-controlled incubator (ca. 95% relative humidity) at 4°, 8°, 15° or 37° C. for 6 h. Non-adherent bacteria were removed by vacuum aspiration after 6 h of incubation and replaced with 0.1 ml of fresh TSB. The stainless steel coupons were reincubated at the same temperature and the media were replaced every 7, 3, 3 and 1 days for incubation at 4°, 8°, 15° or 37° C., respectively. At each sampling time, selected coupons in duplicate were transferred to a laminar flow hood in which weakly adherent bacteria were removed by washing the marked area of each coupon 3 times with PBS, then removing the remaining liquid from the marked area by vacuum aspiration. Each coupon was placed in a 50-ml centrifuge tube containing 9.9 ml of PBS and 30 glass beads (5 mm, Fisher Scientific, Norcross, Ga.) and agitated by a Vortex mixer (Fisher Scientific) for 2 min to disrupt bacteria in the adherent biofilm. The suspended bacteria were serially diluted (1:10) in 0.1% peptone and plated in duplicate on TSA for enumeration of competitive microorganisms or total bacteria (if *L. monocytogenes* counts on MOX were greater than or equal to the bacterial counts on TSA) and MOX for *L. monocytogenes*. The plates were incubated for 48 h at about 37° C. and competitive microorganism and *L. monocytogenes* counts were determined. Coupons inoculated with only $10^{2.6}$-$10^{4.6}$ *L. monocytogenes* served as positive controls, whereas coupons inoculated only with $10^{6.6}$-$10^{8.4}$ competitive microorganisms served as negative controls. Results reported were the average of duplicate determinations.

Identification of nisA and nisB competitive microorganisms: A polymerase chain reaction (PCR) method was used to identify competitive microorganisms that encode NisA and NisB. Bacterial DNA was extracted using a microbial genomic DNA isolation kit according to the protocol described by the manufacturer (Mo Bio Laboratories, Solana Beach, Calif.). The oligonucleotide sequences of the primers used for nisA were 5-CGGCTCTGATTAAATTCTGAAG (SEQ ID NO:1) and 5-CGGTTGAGCTTAAATGAAC (SEQ ID NO:2) and for nisB were 5-AGAGAAGTTATTTACGAT-CAAC (SEQ ID NO:3) and 5-ATCTGACAA-CAAATCTTTTTGT (SEQ ID NO:4). PCR was perfonned with an Icycler 96 Well Reaction Module (Bio-Rad Laboratories, Hercules, CA) according to the procedure described by Olasupo, N. A., U. Schillinger, A. Narbag, H. Dodd, and W. H. Holzapfel, Occurrence of nisin Z production in Lactococcus lactis BFE 1500 isolated from wara, a traditional Nigerian cheese product. Int. J. Food Mirobiol. 53:141-152 (1999) incorporated herein by reference.

Results

A total of 12 biofilms from floor drains of four different food processing facilities were screened for microorganisms inhibitory to *L. monocytogenes*. A total of 156 yeast and 257 bacterial isolates were obtained from the biofilms and assayed for antagonistic activity against *L. monocytogenes*. Twenty-four isolates, including 3 yeasts and 21 bacteria, were inhibitory to *L. monocytogenes* (0.5 to 3.5 mm zones of inhibition), with no bacteria and 3 yeasts identified by the spot-on-lawn assay and 21 bacteria and no yeast identified by the double-layer assay.

All isolates antagonistic to *L. monocytogenes* were evaluated individually for their ability to inhibit growth or inactivate a 5-strain mixture of *L. monocytogenes* in TSB at about 37° C. Under these conditions, two yeast isolates were weakly antagonistic to *L. monocytogenes*, repressing growth of listeriae by 0.7 $\log_{10}$ cfu/ml compared to the positive control of *L. monocytogenes* only. In contrast, nine of the biologically pure bacterial isolates were strongly antagonistic to *L. monocytogenes*, with each providing a greater than 5 $\log_{10}$ cfu/ml differential at 24 h when compared with the *L. monocytogenes*-only positive control as shown in Table 1 below. Four of these bacterial isolates are deposited with the American Type Culture Collection, located at 10801 University Blvd, Manassas, Va. 20110-2209, on Oct. 15, 2002. In particular, the following microorganisms are deposited with the ATCC, *Enterococcus durans* 141-1 having ATCC accession number PTA-4758, *Enterococcus durans* 152 having ATCC accession number PTA-4759, *Lactococcus lactis* C-1-92 having ATCC accession number PTA-4760, or *Lactococcus lactis* C-1-152 having ATCC accession number PTA-4761.

TABLE 1

Inhibition at about 37° C. of *L. monocytogenes* (LM) by competitive microorganism (CM) in tryptic soy broth

| | *L. monocytogenes* or competitive microorganism count ($\log_{10}$ cfu/ml) | | | | | | | | |
|---|---|---|---|---|---|---|---|---|---|
| | 0 time | | | 8 h | | | 24 h | | |
| Isolate No. | LM only[a] | LM + CM[b] | CM only[c] | LM only | LM + CM | CM only | LM only | LM + CM | CM only |
| Bacteria | | | | | | | | | |
| C-2-101 | 3.0 | 3.0 | 5.7 | 6.7 | 6.4 | 7.4 | 9.4 | 9.0 | 8.4 |
| C-1-152 | 3.0 | 2.8 | 6.3 | 6.4 | 5.3 | 9.1 | 9.8 | 7.8 | 9.2 |
| C-2-188 | 3.5 | 2.7 | 6.5 | 6.4 | 6.7 | 6.5 | 9.1 | 9.3 | 7.7 |
| C-1-92 | 3.3 | 3.2 | 6.0 | 6.3 | <0.7[d] | 9.5 | 9.3 | 0.7 | 9.3 |
| 143 | 3.2 | 2.9 | 6.1 | 6.5 | 1.7 | 9.1 | 8.8 | <0.7 | 9.3 |
| 375-1 | 3.0 | 2.9 | 5.8 | 6.7 | 2.2 | 9.4 | 9.5 | 2.8 | 9.4 |
| 129 | 2.8 | 3.0 | 6.4 | 6.6 | 5.2 | 9.2 | 9.4 | 8.5 | 9.4 |

TABLE 1-continued

Inhibition at about 37° C. of *L. monocytogenes* (LM) by competitive microorganism (CM) in tryptic soy broth

| | *L. monocytogenes* or competitive microorganism count ($\log_{10}$ cfu/ml) | | | | | | | | |
|---|---|---|---|---|---|---|---|---|---|
| | 0 time | | | 8 h | | | 24 h | | |
| Isolate No. | LM only[a] | LM + CM[b] | CM only[c] | LM only | LM + CM | CM only | LM only | LM + CM | CM only |
| 123 | 3.5 | 3.3 | 6.3 | 6.7 | 6.5 | 8.2 | 9.2 | 9.0 | 9.6 |
| B-2-18 | 3.3 | 3.2 | 5.7 | 6.7 | 5.8 | 9.1 | 9.4 | 7.6 | 9.6 |
| 152 | 3.6 | 3.4 | 6.2 | 6.7 | 2.4 | 9.1 | 8.7 | 3.3 | 9.5 |
| 141 | 3.5 | 3.4 | 6.0 | 7.9 | 3.5 | 8.8 | 9.5 | 3.1 | 9.1 |
| 123 | 3.2 | 3.2 | 6.0 | 6.4 | 6.6 | 8.5 | 9.0 | 9.2 | 9.7 |
| 147 | 3.2 | 3.2 | 6.1 | 7.6 | 2.7 | 9.4 | 9.4 | 3.6 | 9.3 |
| 375-3 | 2.9 | 2.8 | 5.8 | 5.7 | 5.9 | 7.7 | 9.3 | 6.9 | 9.4 |
| 107 (tiny) | 3.0 | 3.1 | 6.1 | 6.7 | 6.1 | 8.6 | 9.6 | 6.7 | 9.0 |
| 123 | 3.2 | 3.2 | 6.3 | 6.7 | 6.2 | 8.2 | 9.6 | 8.3 | 9.6 |
| 375-2 | 3.3 | 3.1 | 6.3 | 6.4 | 2.0 | 9.4 | 9.4 | 3.1 | 9.3 |
| 107 | 3.3 | 3.2 | 6.0 | 7.2 | 6.4 | 7.8 | 9.4 | 7.7 | 9.2 |
| 141 (2) | 3.1 | 3.0 | 6.3 | 7.4 | 3.1 | 9.1 | 9.6 | 3.8 | 9.6 |
| 143 (2) | 3.2 | 3.2 | 7.0 | 7.5 | 3.4 | 9.3 | 9.3 | 4.0 | 9.3 |
| 107 (2) | 3.2 | 3.2 | 6.0 | 7.3 | 6.8 | 8.2 | 9.0 | 6.7 | 9.4 |
| Yeast | | | | | | | | | |
| C-2-45 | 2.6 | 2.6 | 4.5 | 6.7 | 5.5 | 6.6 | 9.6 | 9.6 | 7.6 |
| C-2-187 | 2.7 | 2.7 | 4.4 | 5.7 | 5.3 | 6.9 | 9.9 | 9.2 | 7.8 |
| C-3-53 | 2.9 | 2.7 | 5.6 | 7.0 | 5.6 | 7.2 | 10.0 | 9.3 | 7.8 |

[a]LM only = *L. monocytogenes* count
[b]LM + CM = *L. monocytogenes* count
[c]CM only = Competitive microorganism count
[d]Minimum detection limit 0.7 $\log_{10}$ cfu/ml Twelve isolates were assayed under the same conditions, but at about 15° C. Three of the isolates were highly antagonistic to *L. monocytogenes*, with greater than a 4 $\log_{10}$ *L. monocytogenes* differential at day 7 compared to *L. monocytogenes*-only positive control, and one isolate, C-1-92, was exceptionally bactericidal, with no detectable *L. monocytogenes* present (>8 $\log_{10}$ *L. monocytogenes*/ml differential compared with positive control) at 7 and 14 days, see Table 2 below.

TABLE 2

Inhibition at about 15° C. of *L. monocytogenes* (LM) by competitive microorganisms (CM) in tryptic soy broth

| | *L. monocytogenes* or competitive microorganism count ($\log_{10}$ cfu/ml) at day | | | | | | | | | | | | | | |
|---|---|---|---|---|---|---|---|---|---|---|---|---|---|---|---|
| | 0 time | | | 1 d | | | 2 d | | | 7 d | | | 14 d | | |
| Isolate No | LM Only[a] | LM + CM[b] | CM only[c] | LM only | LM + CM | CM only | LM only | LM + CM | CM only | LM only | LM + CM | CM only | LM only | LM + CM | CM only |
| 141 | 3.4 | 3.4 | 6.2 | 6.8 | 5.4 | 8.8 | 9.8 | 2.9 | 9.6 | 9.7 | 8.4 | 9.6 | 9.0 | 9.1 | 8.4 |
| 141-2 | 3.4 | 3.4 | 6.2 | 7.3 | 2.7 | 9.6 | 9.7 | 2.8 | 9.6 | 9.8 | 7.2 | 9.8 | 9.0 | 7.6 | 9.8 |
| B-2-18 | 3.5 | 3.3 | 6.7 | 7.2 | 6.3 | 9.6 | 9.8 | 7.2 | 9.9 | 9.4 | 8.0 | 10.2 | 9.6 | 8.0 | 10.2 |
| 152 | 3.4 | 3.4 | 6.2 | 7.2 | 6.0 | 9.1 | 9.8 | 4.1 | 9.4 | 9.7 | 7.3 | 9.4 | 9.1 | 8.6 | 9.4 |
| 143-2 | 3.5 | 3.4 | 5.5 | 7.4 | 7.2 | 8.8 | 9.8 | 4.7 | 9.5 | 9.6 | 8.5 | 9.7 | 8.8 | 8.1 | 9.6 |
| 147 | 3.5 | 3.4 | 6.3 | 7.5 | 2.6 | 9.4 | 9.9 | 2.4 | 9.6 | 9.7 | 7.4 | 9.7 | 9.3 | 8.5 | 9.7 |
| 375-2 | 3.6 | 3.3 | 6.4 | 7.8 | 2.3 | 9.5 | 9.9 | 3.0 | 9.8 | 9.9 | 6.6 | 9.5 | 8.7 | 7.7 | 9.9 |
| 129 | 3.5 | 3.2 | 5.5 | 6.6 | 5.5 | 9.8 | 10.3 | 5.1 | 9.8 | 9.6 | 6.9 | 9.3 | 9.0 | 8.6 | 6.9 |
| C-1-92 | 3.4 | 3.3 | 6.4 | 8.0 | 1.7 | 9.9 | 10.2 | 1.0 | 9.8 | 9.2 | <0.7[d] | 9.2 | 9.0 | <0.7 | 7.8 |
| 375-1 | 3.4 | 3.4 | 6.3 | 6.5 | 6.2 | 9.1 | 9.7 | 3.0 | 9.7 | 9.3 | 3.8 | 9.4 | 9.1 | 7.2 | 9.8 |
| C-1-152 | 3.5 | 3.4 | 6.3 | 7.9 | 7.1 | 9.4 | 9.9 | 8.0 | 9.5 | 9.7 | 8.2 | 9.3 | 9.0 | 9.5 | 9.4 |
| 143 | 3.6 | 3.4 | 6.4 | 7.2 | 7.0 | 8.0 | 9.7 | 3.5 | 9.5 | 8.3 | 4.1 | 9.3 | 8.5 | 7.6 | 9.5 |

[a]LM only = *L. monocytogenes* count
[b]LM + CM = *L. monocytogenes* count
[c]CM only = Competitive microorganism count
[d]Minimum detection limit 0.7 $\log_{10}$ cfu/ml These same twelve isolates were assayed for antagonistic activity to *L. monocytogenes* in TSB at about 8° C. Six of isolates were highly inhibitory, with greater than a 4 $\log_{10}$ *L. monocytogenes*/ml differential at 14 days compared to the *L. monocytogenes* only positive control, and one isolate, 152, was exceptionally antimicrobial, with a 6.3 $\log_{10}$ *L. monocytogenes*/ml differential at 21 days, see Table 3 below.

TABLE 3

Inhibition at about 8° C. of *L. monocytogenes* (LM) by competitive microorganisms (CM) in tryptic soy broth

*L. monocytogenes* or competitive microorganism count ($\log_{10}$ cfu/ml)

| Isolate No. | 0 time | | | 1 d | | | 7 d | | | 14 d | | | 21 d | | |
|---|---|---|---|---|---|---|---|---|---|---|---|---|---|---|---|
| | LM only[a] | LM + CM[b] | CM only[c] | LM only | LM + CM | CM only | LM only | LM + CM | CM only | LM only | LM + CM | CM only | LM only | LM + CM | CM only |
| Bacteria | | | | | | | | | | | | | | | |
| 141 | 3.3 | 3.3 | 6.1 | 4.0 | 4.0 | 6.4 | 8.9 | 4.4 | 9.3 | 9.8 | 5.2 | 9.5 | 9.8 | 6.4 | 9.4 |
| 141-2 | 3.4 | 3.3 | 6.3 | 3.7 | 3.8 | 6.3 | 8.5 | 5.0 | 9.2 | 9.7 | 5.3 | 9.4 | 9.8 | 7.6 | 9.5 |
| B-2-18 | 3.3 | 3.5 | 6.7 | 4.2 | 4.2 | 7.0 | 8.9 | 7.4 | 9.1 | 9.8 | 9.0 | 9.0 | 9.3 | 8.7 | 9.4 |
| 152 | 3.3 | 3.2 | 6.2 | 4.2 | 4.0 | 6.6 | 9.0 | 2.7 | 9.1 | 9.9 | 2.9 | 9.3 | 9.8 | 3.5 | 9.4 |
| 143-2 | 3.2 | 3.1 | 6.4 | 3.7 | 3.5 | 6.4 | 8.0 | 6.0 | 8.3 | 9.4 | 6.4 | 8.9 | 9.5 | 8.0 | 9.1 |
| 147 | 3.5 | 3.5 | 6.4 | 3.7 | 3.8 | 6.2 | 8.5 | 7.3 | 9.2 | 9.4 | 9.2 | 9.4 | 9.5 | 8.9 | 9.5 |
| 375-2 | 3.3 | 3.2 | 6.3 | 4.2 | 3.5 | 6.4 | 9.3 | 3.2 | 9.1 | 9.8 | 5.5 | 9.2 | 9.8 | 7.5 | 9.5 |
| 129 | 3.3 | 3.1 | 5.2 | 3.5 | 3.8 | 6.3 | 9.3 | 6.9 | 8.9 | 9.8 | 6.9 | 9.2 | 9.8 | 7.5 | 9.2 |
| C-1-92 | 3.5 | 3.4 | 6.3 | 3.7 | 3.5 | 6.0 | 9.1 | 5.7 | 8.3 | 9.8 | 5.3 | 8.8 | 9.9 | 5.1 | 8.8 |
| 375-1 | 3.5 | 3.5 | 6.3 | 3.9 | 3.9 | 6.4 | 9.5 | 4.6 | 9.1 | 9.7 | 4.7 | 9.1 | 9.8 | 6.5 | 9.3 |
| C-1-152 | 3.2 | 3.3 | 6.4 | 4.0 | 4.0 | 6.4 | 8.9 | 5.6 | 9.4 | 9.7 | 6.7 | 9.3 | 9.8 | 7.9 | 9.4 |
| 143 | 3.2 | 2.6 | 6.1 | 3.7 | 3.5 | 7.0 | 9.5 | 5.2 | 8.4 | 9.8 | 6.9 | 9.2 | 9.7 | 7.9 | 9.4 |
| Yeast | | | | | | | | | | | | | | | |
| C-2-45 | 2.3 | 2.5 | 5.7 | 3.2 | 3.1 | 5.4 | 8.1 | 8.1 | 7.7 | 9.6 | 9.1 | 7.8 | 9.8 | 9.4 | 7.9 |
| C-3-53 | 2.5 | 2.7 | 5.8 | 3.4 | 3.2 | 5.6 | 8.1 | 8.2 | 8.0 | 9.9 | 7.8 | 6.3 | 9.8 | 9.2 | 8.1 |
| C-2-187 | 2.2 | 2.3 | 4.7 | 2.7 | 2.8 | 4.4 | 8.5 | 7.3 | 5.1 | 9.7 | 9.3 | 7.7 | 9.8 | 9.7 | 6.5 |

[a] LM only = *L. monocytogenes* count
[b] LM + CM = *L. monocytogenes* count
[c] CM only = Competitive microorganism count Nine isolates with antagonistic activity to *L. monocytogenes* at all three temperatures were assayed for their activity against *L. monocytogenes* at about 4° C. Three isolates were highly antagonistic, with greater than a 4 $\log_{10}$ *L. monocytogenes*/ml differential at 28 days compared to the positive control, and one isolate, 152, was exceptionally antimicrobial, with a 6 $\log_{10}$ differential at 28 days, see Table 4 below.

TABLE 4

Inhibition at about 4° C. of *L. monocytogenes* (LM) by competitive microorganisms (CM) in tryptic soy broth

*L. monocytogenes* or competitive microorganism count ($\log_{10}$ cfu/ml)

| Isolate No. | 0 time | | | 7 d | | | 14 d | | | 21 d | | | 28 d | | |
|---|---|---|---|---|---|---|---|---|---|---|---|---|---|---|---|
| | LM only[a] | LM + CM[b] | CM only[c] | LM only | LM + CM | CM only | LM only | LM + CM | CM only | LM only | LM + CM | CM only | LM only | LM + CM | CM only |
| 141-1 | 2.7 | 2.6 | 5.0 | 4.2 | 4.1 | 5.6 | 6.0 | 6.5 | 6.5 | 8.6 | 6.6 | 8.2 | 9.5 | 6.3 | 8.7 |
| 152 | 3.4 | 3.4 | 6.4 | 4.1 | 3.7 | 6.6 | 7.0 | 4.3 | 7.5 | 8.5 | 4.5 | 8.7 | 9.9 | 3.9 | 9.2 |
| C-1-92 | 3.5 | 3.0 | 6.5 | 4.1 | 3.7 | 5.9 | 6.9 | 5.8 | 5.7 | 8.2 | 6.7 | 5.0 | 9.9 | 8.0 | 5.3 |
| 143-1 | 2.9 | 2.5 | 5.0 | 3.3 | 3.3 | 5.2 | 6.7 | 5.9 | 5.2 | 8.0 | 7.5 | 6.4 | 9.5 | 8.3 | 6.9 |
| C-1-152 | 2.7 | 2.9 | 5.9 | 3.7 | 3.5 | 5.6 | 6.5 | 6.1 | 6.6 | 8.3 | 7.1 | 7.3 | 9.5 | 7.4 | 8.4 |
| 375-1 | 2.8 | 2.4 | 5.2 | 4.2 | 3.8 | 5.4 | 7.0 | 6.4 | 6.7 | 8.4 | 7.2 | 8.0 | 9.7 | 7.3 | 8.6 |
| 143-2 | 3.3 | 3.2 | 5.9 | 4.2 | 3.3 | 6.4 | 6.8 | 4.9 | 7.3 | 8.3 | 5.0 | 8.2 | 9.3 | 5.4 | 8.8 |
| 141-2 | 3.2 | 3.2 | 6.1 | 4.0 | 3.7 | 6.4 | 6.8 | 4.9 | 7.2 | 8.0 | 5.2 | 8.0 | 9.4 | 5.4 | 8.9 |
| 375-2 | 3.4 | 3.3 | 6.4 | 4.1 | 3.6 | 6.4 | 6.3 | 4.5 | 6.8 | 8.0 | 5.0 | 8.4 | 9.0 | 5.0 | 9.0 |

[a] LM only = *L. monocytogenes* count
[b] LM + CM = *L. monocytogenes* count
[c] CM only = Competitive microorganism count As previously indicated, identification of the nine most antagonistic cultures revealed that six (isolates no. 141-1, 141-2, 143-2, 152, 375-1 and 375-2) were *Enterococcus durans* and 16S rRNA analysis indicated all are indistinguishable; two (isolates no. C-1-92 and C-1-152) were *Lactococcus lactis* subsp. *lactis*; and one (isolate no. 143-1) was *Lactobacillus plantarum*. *L. lactis* subsp. *lactis* C-1-92 encoded both nisA and nisB, but none of the other competitive microorganisms evaluated encoded either nisA or nisB.

The nine antagonistic bacterial isolates and two yeast isolates were evaluated at about 37° C. at two different cell number combinations (highest level at 6.9 (for yeast) or 8.3-8.4 (for bacteria) $\log_{10}$ competitive microorganisms/cm$^2$ and 4.6 $\log_{10}$ *L. monocytogenes*/cm$^2$; and lower level at 6.4-6.5 $\log_{10}$ competitive microorganisms/cm$^2$ and 2.9 $\log_{10}$ *L. monocytogenes*/cm$^2$) for their ability to control *L. monocytogenes* in biofilms on stainless steel coupons. Results of studies with the highest combination of microbial populations revealed a more than 6 $\log_{10}$ *L. monocytogenes*/cm$^2$ (to an undetectable level by a direct plating method; <1.7 $\log_{10}$ cfu/cm$^2$) differential compared to the positive control for eight isolates at 37° C. for 24 h and a 3 to 5 $\log_{10}$ *L. monocytogenes*/cm$^2$ differential for one isolate, see Table 5 below. There was only a 0.2-0.9 $\log_{10}$ *L. monocytogenes*/cm$^2$ differential for the two yeast isolates (see Table 5 below). Studies with a lower combination of microbial populations resulted in all nine competitive bacterial isolates providing a greater than a 6 $\log_{10}$ *L. monocytogenes*/cm$^2$ differential compared to the *L. monocytogenes*-only positive control, see Table 6 below.

Six competitive bacterial isolates were evaluated under similar conditions (initial cell populations of 3.7 $\log_{10}$ *L. monocytogenes*/cm$^2$ and 6.3-6.5 $\log_{10}$ competitive microorganisms/cm$^2$) at about 15° C., of which two isolates, *L. lactis* subsp. *lactis* C-1-92 and C-1-152, controlled *L. monocytogenes* to an undetectable level (>7.8 $\log_{10}$ *L. monocytogenes*/cm$^2$ differential) through 28 days, which was the end of the study, see Table 7 below.

TABLE 6

Inhibition at about 37° C. of *L. monocytogenes* (LM) by competitive microorganism (CM) in biofilms formed on stainless steel coupons

| | *L. monocytogenes* or competitive microorganism count ($\log_{10}$ cfu/cm$^2$) | | | | | |
|---|---|---|---|---|---|---|
| | 0 time | | | 24 h | | |
| Isolate No. | LM only[a] | LM + CM[b] | CM only[c] | LM only | LM + CM | CM only |
| 141-1 | 2.9 | 2.9 | 6.5 | 7.7 | <1.7[d] | 7.9 |
| 152 | 2.9 | 2.9 | 6.6 | 7.7 | <1.7 | 7.8 |
| 143-1 | 2.9 | 2.9 | 6.4 | 7.7 | <1.7 | 7.3 |
| C-1-152 | 2.9 | 2.9 | 6.4 | 7.7 | <1.7 | 7.8 |
| 375-1 | 2.9 | 2.9 | 6.4 | 7.7 | <1.7 | 8.0 |
| 143-2 | 2.9 | 2.9 | 6.5 | 7.7 | <1.7 | 8.0 |
| 141-2 | 2.9 | 2.9 | 6.5 | 7.7 | <1.7 | 7.8 |
| 375-2 | 2.9 | 2.9 | 6.6 | 7.7 | <1.7 | 7.9 |
| C-1-92 | 2.6 | 2.6 | 6.4 | 7.1 | <1.7 | 7.2 |

[a] LM only = *L. monocytogenes* count
[b] LM + CM = *L. monocytogenes* count
[c] CM only = Competitive microorganism count
[d] Minimum detection limit 1.7 $\log_{10}$ cfu/cm$^2$

TABLE 5

Inhibition at about 37° C. of *L. monocytogenes* (LM) by competitive microorganisms (CM) in biofilms formed on stainless steel coupons

| | *L. monocytogenes* or competitive microorganism count ($\log_{10}$ cfu/cm$^2$) | | | | | | | | | | | |
|---|---|---|---|---|---|---|---|---|---|---|---|---|
| | Trial No. 1 | | | | | | Trial No. 2 | | | | | |
| | 0 time | | | 24 h | | | 0 time | | | 24 h | | |
| Isolate No. | LM Only[a] | LM + CM[b] | CM only[c] | LM only | LM + CM | CM only | LM only | LM + CM | CM only | LM only | LM + CM | CM only |
| Bacteria | | | | | | | | | | | | |
| 141-1 | 4.6 | 4.6 | 8.3 | 7.8 | <1.7[d] | 7.5 | 4.6 | 4.6 | 8.3 | 7.8 | <1.7[d] | 7.2 |
| 152 | 4.6 | 4.6 | 8.4 | 7.8 | <1.7 | 7.6 | 4.6 | 4.6 | 8.3 | 7.8 | <1.7 | 7.7 |
| C-1-92 | 4.6 | 4.6 | 8.4 | 7.8 | <1.7 | 6.6 | 4.6 | 4.6 | 8.4 | 7.8 | <1.7 | 7.3 |
| 143-1 | 4.6 | 4.6 | 8.3 | 7.8 | 2.7 | 7.0 | 4.6 | 4.6 | 8.3 | 7.8 | 4.2 | 7.1 |
| C-1-152 | 4.6 | 4.6 | 8.4 | 7.8 | <1.7 | 7.1 | 4.6 | 4.6 | 8.4 | 7.8 | <1.7 | 7.4 |
| 375-1 | 4.6 | 4.6 | 8.3 | 7.8 | <1.7 | 7.3 | 4.6 | 4.6 | 8.3 | 7.8 | <1.7 | 7.7 |
| 143-2 | 4.6 | 4.6 | 8.4 | 7.8 | <1.7 | 6.9 | 4.6 | 4.6 | 8.4 | 7.8 | <1.7 | 7.4 |
| 141-2 | 4.6 | 4.6 | 8.4 | 7.8 | <1.7 | 7.4 | 4.6 | 4.6 | 8.4 | 7.8 | <1.7 | 7.3 |
| 375-2 | 4.6 | 4.6 | 8.4 | 7.8 | <1.7 | 7.4 | 4.6 | 4.6 | 8.4 | 7.8 | <1.7 | 7.5 |
| Yeast | | | | | | | | | | | | |
| C-2-45 | 4.6 | 4.6 | 6.9 | 7.8 | 7.3 | 5.0 | 4.6 | 4.6 | 6.9 | 7.8 | 7.4 | 7.2 |
| C-3-53 | 4.6 | 4.6 | 6.9 | 7.8 | 7.6 | 7.3 | 4.6 | 4.6 | 6.9 | 7.8 | 6.9 | 6.3 |

[a] LM only = *L. monocytogenes* count
[b] LM + CM = *L. monocytogenes* count
[c] CM only = Competitive microorganism count
[d] Minimum detection limit 1.7 $\log_{10}$ cfu/cm$^2$

TABLE 7

Inhibition at about 15° C. of *L. monocytogenes* (LM) by competitive microorganisms (CM) in biofilms formed on stainless steel coupons

| | *L. monocytogenes* or competitive microorganism count ($\log_{10}$ cfu/cm$^2$) | | | | | | | | | | | |
|---|---|---|---|---|---|---|---|---|---|---|---|---|
| | 0 time | | | 7 d | | | 14 d | | | 28 d | | |
| Isolate No. | LM only[a] | LM + CM[b] | CM only[c] | LM only | LM + CM | CM only | LM only | LM + CM | CM only | LM only | LM + CM | CM only |
| 141-1 | 3.7 | 3.7 | 6.5 | 8.5 | <1.7[d] | 8.1 | 9.2 | 5.3 | 8.2 | 9.5 | 6.6 | 8.8 |
| 152 | 3.7 | 3.7 | 6.3 | 8.5 | 1.7 | 7.9 | 9.2 | 4.3 | 8.7 | 9.5 | 6.5 | 8.4 |
| 375-1 | 3.7 | 3.7 | 6.4 | 8.5 | 2.7 | 7.7 | 9.2 | 5.3 | 8.7 | 9.5 | 6.6 | 9.0 |
| C-1-92 | 3.7 | 3.7 | 6.6 | 8.5 | <1.7 | 6.7 | 9.2 | <1.7 | 8.6 | 9.5 | <1.7 | 8.5 |
| 143-1 | 3.7 | 3.7 | 6.5 | 8.5 | 4.7 | 7.7 | 9.2 | 2.6 | 7.8 | 9.5 | 6.4 | 9.0 |
| C-1-152 | 3.7 | 3.7 | 6.3 | 8.5 | <1.7 | 7.5 | 9.2 | <1.7 | 6.7 | 9.5 | <1.7 | 8.3 |

[a] LM only = *L. monocytogenes* count
[b] LM + CM = *L. monocytogenes* count
[c] CM only = Competitive microorganism count
[d] Minimum detection limit 1.7 $\log_{10}$ cfu/cm$^2$ The same six competitive bacterial isolates (at initial populations of 6.0-6.7 $\log_{10}$ cfu/cm$^2$) were evaluated in combination with an initial population of 3.7 $\log_{10}$ *L. monocytogenes*/cm$^2$ on stainless steel coupons at about 8° C. Four isolates, *E. durans* 141-1, 152 and 375-1 and *Lc. Lactis* subsp. *lactis* C-1-92, were highly inhibitory to *L. monocytogenes*, with no listeriae detected (>6.8 $\log_{10}$ cfu/cm$^2$ differential) at 21 and 28 days, see Table 8 below.

*genes*, with no detectable *L. monocytogenes* (differentials of >5.1 and >7.0 $\log_{10}$ *L. monocytogenes*/cm$^2$ compared to positive *L. monocytogenes*-only control) at 35 days when either initial population of *L. monocytogenes* was used (see Tables 9 and 10 below). Interestingly, *Lc. lactis* subsp. *lactis* C-1-92 did not grow but rather declined in cell numbers (3.6-3.8 $\log_{10}$ cfu/cm$^2$ reduction) during 35 days at about 4° C., whereas cell populations of all five other competitive microorganisms

TABLE 8

Inhibition at about 8° C. of *L. monocytogenes* (LM) by competitive microorganisms (CM) in biofilms formed on stainless steel coupons

| | *L. monocytogenes* or competitive microorganism count ($\log_{10}$ cfu/cm$^2$) | | | | | | | | | | | | | | |
|---|---|---|---|---|---|---|---|---|---|---|---|---|---|---|---|
| | 0 time | | | 7 d | | | 14 d | | | 21 d | | | 28 d | | |
| Isolate No. | LM[a] only | LM[b] + CM | CM[c] only | LM only | LM + CM | CM only | LM only | LM + CM | CM only | LM only | LM + CM | CM only | LM only | LM + CM | CM only |
| 141-1 | 3.7 | 3.7 | 6.0 | 6.8 | 3.7 | 7.4 | 8.5 | 3.3 | 8.4 | 8.5 | <1.7[d] | 8.0 | 8.8 | <1.7 | 7.7 |
| 152 | 3.7 | 3.7 | 6.4 | 6.8 | 3.9 | 7.5 | 8.5 | 3.5 | 8.2 | 8.5 | <1.7 | 7.6 | 8.8 | <1.7 | 7.8 |
| 375-1 | 3.7 | 3.7 | 6.5 | 6.8 | 3.7 | 7.6 | 8.5 | 3.0 | 8.5 | 8.5 | <1.7 | 7.8 | 8.8 | <1.7 | 7.8 |
| C-1-92 | 3.7 | 3.7 | 6.7 | 6.8 | <1.7 | 4.7 | 8.5 | <1.7 | 6.5 | 8.5 | <1.7 | 5.4 | 8.8 | <1.7 | 4.7 |
| 143-1 | 3.7 | 3.7 | 6.5 | 6.8 | 3.9 | 7.2 | 8.5 | 4.4 | 8.1 | 8.5 | 5.9 | 7.5 | 8.8 | 3.3 | 7.7 |
| C-1-152 | 3.7 | 3.7 | 6.4 | 6.8 | 3.1 | 7.4 | 8.5 | 4.5 | 8.1 | 8.5 | 4.9 | 7.8 | 8.8 | 6.4 | 7.7 |

[a] LM only = *L. monocytogenes* count
[b] LM + CM = *L. monocytogenes* count
[c] CM only = Competitive microorganism count
[d] Minimum detection limit is 1.7 $\log_{10}$ cfu/cm$^2$ Five and six competitive bacterial isolates (at initial populations of 6.3-6.6 $\log_{10}$ cfu/cm$^2$) were evaluated in combination with two initial populations of *L. monocytogenes* 2.6 and 4.3 $\log_{10}$ *L. monocytogenes*/cm$^2$ on stainless coupons held at about 4° C. One competitive isolate *Lc. Lactis* subsp. *lactis* C-1-92 was especially effective in controlling *L. monocyto-* increased by 1 to 2 $\log_{10}$ cfu/cm$^2$ under the same conditions. The other five competitive microorganisms also were inhibitory to *L. monocytogenes* through 35 days at about 4° C., with differentials of *L. monocytogenes* cell populations in biofilms compared to *L. monocytogenes*-only positive controls ranging from 2.0 to >7.0 $\log_{10}$ cfu/cm$^2$.

TABLE 9

Inhibition at about 4° C. of *L. monocytogenes* (LM) by competitive microorganisms (CM) in biofilms formed on stainless steel coupons

*L. monocytogenes* or competitive microorganism count ($\log_{10}$ cfu/cm$^2$)

| | 0 time | | | 14 d | | | 21 d | | | 28 d | | | 35 d | | |
|---|---|---|---|---|---|---|---|---|---|---|---|---|---|---|---|
| Isolate No. | LM only[a] | LM + CM[b] | CM only[c] | LM only | LM + CM | CM only | LM only | LM + CM | CM only | LM only | LM + CM | CM only | LM only | LM + CM | CM only |
| 141-1 | 2.6 | 2.6 | 6.4 | 3.7 | 2.2 | 6.4 | 4.5 | 2.3 | 7.0 | 6.0 | 2.3 | 7.6 | 6.8 | 3.2 | 7.9 |
| 152 | 2.6 | 2.6 | 6.6 | 3.7 | <1.7 | 6.6 | 4.5 | <1.7 | 7.3 | 6.0 | 2.7 | 7.8 | 6.8 | 2.5 | 7.8 |
| 375-1 | 2.6 | 2.6 | 6.5 | 3.7 | 2.2 | 6.2 | 4.5 | 2.2 | 7.0 | 6.0 | <1.7 | 7.3 | 6.8 | 2.4 | 7.8 |
| C-1-92 | 2.6 | 2.6 | 6.3 | 3.7 | <1.7 | 3.8 | 4.5 | <1.7 | 3.9 | 6.0 | <1.7 | 3.5 | 6.8 | <1.7 | 2.5 |
| 143-1 | 2.6 | 2.6 | 6.5 | 3.7 | <1.7 | 5.9 | 4.5 | 2.2 | 6.5 | 6.0 | <1.7 | 6.9 | 6.8 | 3.0 | 7.5 |
| C-1-152 | 2.6 | 2.6 | 6.5 | 3.7 | 2.0 | 6.1 | 4.5 | <1.7 | 6.4 | 6.0 | 2.5 | 7.2 | 6.8 | 3.4 | 7.4 |

[a] LM only = *L. monocytogenes* count
[b] LM + CM = *L. monocytogenes* count
[c] CM only = Competitive microorganism count
[d] Minimum detection limit 1.7 $\log_{10}$ cfu/cm$^2$

TABLE 10

Inhibition at about 4° C. of *L. monocytogenes* (LM) by competitive microorganisms (CM) in biofilms formed on stainless steel coupons

*L. monocytogenes* or competitive microorganism count ($\log_{10}$ cfu/cm$^2$)

| | 0 time | | | 14 d | | | 21 d | | | 28 d | | | 35 d | | |
|---|---|---|---|---|---|---|---|---|---|---|---|---|---|---|---|
| Isolate No. | LM only[a] | LM + CM[b] | CM only[c] | LM only | LM + CM | CM only | LM only | LM + CM | CM only | LM only | LM + CM | CM only | LM only | LM + CM | CM only |
| 141-1 | 4.3 | 4.3 | 6.4 | 3.6 | 1.7 | 6.1 | 5.1 | 3.2 | 6.9 | 6.6 | 2.6 | 7.3 | 8.7 | 2.5 | 8.0 |
| 152 | 4.3 | 4.3 | 6.5 | 3.6 | 3.0 | 6.4 | 5.1 | <1.7[d] | 6.9 | 6.6 | <1.7 | 7.6 | 8.7 | <1.7 | 8.3 |
| C-1-92 | 4.3 | 4.3 | 6.5 | 3.6 | <1.7 | 4.3 | 5.1 | 2.9 | 3.9 | 6.6 | 2.0 | 3.5 | 8.7 | <1.7 | 2.9 |
| 143-1 | 4.3 | 4.3 | 6.5 | 3.6 | 3.0 | 6.1 | 5.1 | 1.7 | 6.6 | 6.6 | 4.5 | 7.0 | 8.7 | 4.8 | 7.4 |
| C-1-152 | 4.3 | 4.3 | 6.6 | 3.6 | <1.7 | 6.0 | 5.1 | 3.1 | 6.8 | 6.6 | 1.7 | 7.1 | 8.7 | 6.7 | 7.0 |

[a] LM only = *L. monocytogenes* count
[b] LM + CM = *L. monocytogenes* count
[c] CM only = Competitive microorganism count
[d] Minimum detection limit 1.7 $\log_{10}$ cfu/cm$^2$

DNA Fingerprinting of the Probiotic Bacteria

As shown in FIG. 1, four probiotic isolates deposited with the ATCC, i.e., C-1-92 [*L. lactis* subsp. *lactis*] (lane 2), C-1-152 [*L. lactis* subsp. *lactis*] (lane 3), 141-1 [*E. durans*] (lane 4) and 152 [*E. durans*] (lane 5), were analyzed for their DNA fingerprinting by pulsed field-gel electrophoresis. Strains were grown in Brain Heart Infusion agar (BHIA) at 37° C. for 16-18 h individually. Bacteria were collected by a cotton swab and suspended in 3 ml of TE (10 mM Tris:1 mM EDTA, pH 8.0). Bacterial concentration was adjusted to an OD reading of 1.0 at 600 nm. 240 µl of each bacterial suspension was transferred to a 1.5 ml tube and 60 µl of lysozyme solution was added (10 mg/ml). The tubes were incubated at 37° C. for 10 min and 1.2% SeaKem Gold agarose containing proteinase K (20 mg/ml) was added and mixed with the cell suspension. The melted mixture was transferred to a mold and incubated at room temperature for 15 min to solidify. Plugs were then treated for 2 h at 54° C. in lysis buffer. Following washing, the plugs were digested with 4 µl (40 U/µl) ApaI (Roche Diagnostics Corp., Indianapolis, Ind.) at 30° C. for 16 h and electrophoresed on 1.0% agarose gel in 0.5× Tris-borate-EDTA buffer (0.445 M Tris, 0.0125 M EDTA, and 0.445 M boric acid) with a contour-clamped homogeneous electric field device (CHEF MAPPER, Bio-Rad, Hercule, Calif.). After electrophoresis for 20 h at 6 V/cm with pulse times of 4 to 40.01 s at 14° C., the gels were stained with ethidium bromide, and the bands were visualized and photographed with UV transillumination (See FIG. 1).

As discussed above, *L. monocytogenes* can attach through biofilms to various types of surfaces including stainless steel, glass, and rubber. Biofilms, which entrap and protect *L. monocytogenes* from disinfectants, have been documented in meat and dairy processing plant environments. Furthermore, it is well documented that strains of *L. monocytogenes* can become well established in a food processing environment and remain members of the resident microbial flora for many years. As indicated above, the present disclosure describes the isolation and characterization of a number of microorganisms that (i) thrive in combination with *L. monocytogenes* within a biofilm at a wide range of temperatures that occur in food processing facilities (especially under refrigeration conditions) and (ii) compete to inhibit listeriae growth. In particular, initial screening identified 24 promising candidates with anti-listerial activity. Further competitive testing between the candidate microorganisms and *L. monocytogenes* in broth and in biofilms at different temperatures identified nine bacterial isolates that effectively reduced, controlled, or eliminated detectable *L. monocytogenes* depending on environmental conditions. One strain in particular, *Lc. lactis* subsp. *lactis* C-1-92, was especially effective in controlling *L. monocytogenes* when in biofilms for extended periods of time, including at about 4° C. This strain uniquely produced nisin A and nisin B, which are inhibitory to *L. monocytogenes*. Two other isolates, *Entercoccus durans* 141-1 and 152, also were very effective in controlling *L. monocytogenes* in biofilms. These isolates (*E. durans* 141-1 and 152) grow at refrigeration temperatures and have antagonistic activity to *L. monocytogenes* under refrigeration conditions. These strains are useful in food processing locations that require a low temperature environment such as for processing ready-to-eat foods.

Application of Probiotic Bacteria in Ready-to-Eat Meat for Reduction of *L. monocytogenes*

Three probiotic bacteria, including C-1-92 (*Lactococcus lactis* subsp. *lactis*), C-1-152 (*Lactococcus lactis* subsp. *lactis*), and 143 (*Lactobacillus plantarum*) were evaluated for their effect to control *L. monocytogenes* in ready-to-eat meat at a population of $10^6$ cfu/cm$^2$. A 5-strain mixture of *L. monocytogenes* (LM113, LM51779, LM112, LM9666 and LM101) including serotype 1/2a, 1/2b and 4b was used as the inoculum. Frankfurters purchased from a local retail store were tested.

Frankfurters were immersed first in a suspension of probiotic bacteria ($10^6$ cfu/ml) for 30 seconds and dried in a laminar flow hood for 20 minutes, and then immersed in the suspension of *L. monocytogenes* ($10^4$ cfu/ml) according to the same procedure.

Two storage temperatures, 4° C. and 8° C., were evaluated. Following inoculation, each frankfurter was individually sealed in a Ziploc bag, held at 4 and 8° C., and sampled at weekly intervals for the shelf life of the product as determined by the use of the date printed on the label. Samples were placed in a Whirl-Pak bag containing 10 ml of 0.1% peptone. The bags were agitated on a shaker at 200 rpm for 2 min with intermittent massaging by hands. Sample suspensions were serially diluted (1:10) in 0.1% peptone and a volume of 0.1 ml from each dilution tube was inoculated in duplicate onto modified Oxford agar (MOX) and tryptic soy agar (TSA) plates. The plates were incubated for 24 h at 37° C. Typical colonies (black) on MOX were enumerated as *L. monocytogenes*.

Results indicated that at 4° C. the treatment by probiotic bacteria reduced the population of *L. monocytogenes* from 0.7 to 0.8 log$_{10}$ cfu/cm$^2$ (see Table 11 below) and at 8° C. either kept the population at the same level or reduced the population of *L. monocytogenes* from 0.1 to 0.3 log$_{10}$ cfu/cm$^2$ (see Table 12 below) depending on different combinations at the end of the experiment when compared with the population at the beginning.

TABLE 11

*L. monocytogenes* counts on frankfurters with and without combinations of probiotic bacteria held at 4° C.

| Treatment | Microbial count (log$_{10}$ cfu/cm$^2$) at week: | | | | | | |
|---|---|---|---|---|---|---|---|
| | 0 | 1 | 2 | 3 | 4 | 5 | 8 |
| L. M. only | 3.8 | 3.9 | 4.0 | 4.2 | 4.5 | 4.3 | 4.2 |
| C-1-92 & 143 + L. M.$^a$ | 3.5 | 3.1 | 2.7 | 2.8 | 2.7 | 3.2 | 2.7 |
| C-1-92 & C-1-152 + L. M. | 3.6 | 2.8 | 4.2 | 3.1 | 3.1 | 3.0 | 2.9 |
| 143 & C-1-152 + L. M. | 3.6 | 3.2 | 3.0 | 3.2 | 3.2 | 3.0 | 2.9 |
| C-1-92 & 143 & C-1-152 + L. M. | 3.8 | 3.0 | 2.7 | 3.0 | 3.1 | 3.0 | 3.0 |

$^a$L. M. = *Listeria monocytogenes*.

TABLE 12

*L. monocytogenes* counts on frankfurters with and without combinations of probiotic bacteria held at 8° C.

| Treatment | Microbial count (log$_{10}$ cfu/cm$^2$) at week: | | | | | |
|---|---|---|---|---|---|---|
| | 0 | 1 | 2 | 3 | 4 | 5 |
| L. M.$^a$ only | 3.8 | 4.5 | 4.4 | 4.7 | 4.8 | 6.9 |
| C-1-92 & 143 + L. M. | 3.5 | 4.2 | 2.8 | 4.0 | 3.5 | 3.8 |
| C-1-92 & C-1-152 + L. M. | 3.6 | 3.7 | 3.1 | 3.6 | 3.8 | 3.7 |
| 143 & C-1-152 + L. M. | 3.6 | 3.2 | 2.8 | 3.1 | 4.4 | 3.7 |
| C-1-92 & 143 & C-1-152 + L. M. | 3.8 | 4.2 | 2.9 | 3.2 | 3.5 | 3.8 |

$^a$L. M. = *Listeria monocytogenes*.

Application of Probiotic Bacteria in Floor Drains for Reduction/Elimination of *L. monocytogenes* in a Poultry Processing Plant Two probiotic bacteria, C-1-92 (*Lactococcus lactis* subsp. *lactis*) and 152 (*Enterococcus durans*) were selected as the treatment strains and a poultry processing plant was selected for the field trial. Five floor drains in the plant at temperatures ranging from 0.3 to 29° C. were selected for microbiological observation.

Before the treatment these floor drains were evaluated every two weeks for five times plus one time after sanitation in the plant for the baseline determination of *L. monocytogenes* and aerobic bacterial count. Whirl-Pak "speci-sponge" bags (Nasco, Fort Atkinson, Wis.) were used for collection of the samples. Sterilized gloves were worn during the collection and processing of the samples so as to prevent cross-contamination. Samples from five locations in and around each floor drain were collected. These locations included (i) fluid from the drain, (ii) the right side of the drain, (iii) the left side of the drain, (iv) inside of the drain (3.8×7.6 cm), and (v) the surface of the floor within 1 foot of the drain. The samples were kept at 5° C. and transported to the laboratory within 12 h and assayed within 72 h. A 10 ml volume of brain heart infusion (Becton Dickinson Microbiological Systems, Sparks, Md.) was added into each bag. The bag was individually pummeled in a stomacher for 1 min at about 130 RPM. The samples were then serially (1:10) diluted in 0.1% peptone to $10^{-8}$ cfu/ml. A 0.1 ml volume from each dilution tube was plated on the surface of Modified Oxford medium (MOX, Oxford Ltd., Basingstoke, Hampshire, UK) and plate count agar (PCA, Becton Dickinson) in duplicate. For counting the bacterial number the MOX plates were incubated at 37° C. for 48 h, and PCA plates were incubated at 30° C. for 48 h. Typical *L. monocytogenes* colonies (black) were counted as presumptive *L. monocytogenes*. Up to five colonies from the highest dilution were randomly picked for confirmation of *L. monocytogenes* by a latex precipitation assay (Oxoid).

A population of $10^7$ probiotic bacteria/ml in a one-time application of foam formula were used to treat the floor drain after the sanitation process was finished daily for four times in a first week (Monday through Thursday). Then the treatment was performed twice a week (Tuesday and Thursday) for the next three weeks. Samples were collected once a week for the five weeks after the treatment was started. Bacteria were individually grown in 300 ml Lactobacilli MRS broth (MRS, Becton Dickinson) at 32° C. for 24 h. The bacterial broth was precipitated at 10,000×g for 20 min at 4° C. The bacteria were then resuspended in 25 ml MRS broth at about $10^9$ cfu/ml. A volume of 1 ml was serially (1:10) diluted in 0.1% peptone to $10^{-8}$ cfu/ml. A quantity of 0.1 ml from dilution tubes ($10^{-5}$ to $10^{-8}$) was plated on MRS agar and tryptic soy agar in duplicate for the actual counting of the bacterial number. After arriving at the processing plant, the two isolates (25 ml each), 20 ml of Dy-gest I, 20 ml of Dy-gest II, plus 1 gallon of water were added to the tank foamer (Ecolab, St. Paul, Minn.). After connecting the air supply to the tank foamer, the foam was applied in each floor drain.

Results demonstrated that the average number of *L. monocytogenes* in floor drains sampled at six different times (at two week intervals) in this poultry processing plant before the treatment by probiotic bacteria ranged from 3.3 to 4.0 $\log_{10}$ cfu/cm$^2$ for drain #1, from 4.2 to 5.4 $\log_{10}$ cfu/cm$^2$ for drain #3, from 3.4 to 4.5 $\log_{10}$ cfu/cm$^2$ for drain #4, from 3.2 to 4.2 $\log_{10}$ cfu/cm$^2$ for drain #6, and from 6.1 to 8.2 $\log_{10}$ cfu/cm$^2$ for drain #8 (see Table 13 below).

TABLE 13

The mean and standard deviation of *L. monocytogenes* count ($\log_{10}$ cfu/cm$^2$) from drain samples located at different temperatures and collected at six different times

| Lo-cation | Floor drains | | | | |
|---|---|---|---|---|---|
| | #1 | #3 | #4 | #6 | #8 |
| Drain | 3.3 ± 0.8 | 4.2 ± 1.2 | 4.2 ± 1.1 | 4.2 ± 1.2 | 7.6 ± 1.1 |
| Right side | 3.9 ± 0.7 | 5.0 ± 0.9 | 4.3 ± 0.8 | 3.5 ± 1.9 | 7.6 ± 0.8 |
| Left side | 4.0 ± 1.0 | 4.4 ± 1.3 | 3.4 ± 1.1 | 3.2 ± 1.5 | 8.2 ± 0.5 |
| Inside | 3.5 ± 0.8 | 5.4 ± 1.3 | 4.5 ± 1.1 | 3.6 ± 1.3 | 7.8 ± 0.9 |
| Floor (1 foot) | 3.6 ± 0.9 | 5.3 ± 0.6 | 4.3 ± 1.4 | 3.3 ± 1.3 | 6.1 ± 1.9 |
| Temperature | 21.8 ± 2.9 | 18.6 ± 2.3 | 4.7 ± 1.3 | 5 ± 1.2 | 28.6 ± 0.9 |

After the treatment by these two probiotic bacteria, the average number of *L. monocytogenes* ranged from 1.8 to 2.0 $\log_{10}$ cfu/cm$^2$ for drain #1, 1.9 to 2.8 $\log_{10}$ cfu/cm$^2$ for drain #3, 1.7 to 2.1 $\log_{10}$ cfu/cm$^2$ for drain #4, 1.9 to 2.1 $\log_{10}$ cfu/cm$^2$ for drain #6 and 3.5 to 4.0 $\log_{10}$ cfu/cm$^2$ for drain #8 (see Table 14 below).

TABLE 14

The mean and standard deviation of *L. monocytogenes* count ($\log_{10}$ cfu/cm$^2$) from drain samples collected after probiotic treatment at five different times

| Lo-cation | Floor drains | | | | |
|---|---|---|---|---|---|
| | #1 | #3 | #4 | #6 | #8 |
| Drain | 1.8 ± 0.4 | 1.9 ± 0.3 | 1.9 ± 0.3 | 2.1 ± 0.4 | 4.0 ± 2.0 |
| Right side | 2.0 ± 0.5 | 2.1 ± 0.8 | 1.7 ± 0.1 | 1.9 ± 0.7 | 3.9 ± 2.0 |
| Left side | 2.0 ± 0.6 | 2.3 ± 0.6 | 2.1 ± 1.2 | 1.9 ± 0.4 | 3.9 ± 2.2 |
| Inside | 2.0 ± 0.5 | 2.8 ± 1.4 | 1.7 ± 0.1 | 2.0 ± 0.7 | 3.7 ± 1.8 |
| Floor (1 foot) | 1.9 ± 0.5 | 2.1 ± 0.6 | 2.1 ± 0.9 | 1.9 ± 0.6 | 3.5 ± 0.8 |
| Temperature | 11.7 ± 2.2 | 11.5 ± 2.2 | 0.9 ± 1.0 | 2.5 ± 0.9 | 23.5 ± 1.5 |

Compared with the *L. monocytogenes* counts before the treatment, the average population of *L. monocytogenes* after the probiotic treatment was reduced 1.7 $\log_{10}$ cfu/cm$^2$ for drain #1, 2.6 $\log_{10}$ cfu/cm$^2$ for drain #3, 2.2 $\log_{10}$ cfu/cm$^2$ for drain #4, 1.6 $\log_{10}$ cfu/cm$^2$ for drain #6 and 3.7 $\log_{10}$ cfu/cm$^2$ for drain #8. These results demonstrated that the application of these two probiotic bacteria significantly reduced the population of *L. monocytogenes* in the floor drains located at various temperatures in this poultry processing plant.

Accordingly, in light of the above discussion, it should be appreciated that compositions for, and methods of, treating one or more surfaces of a food processing facility are provided. For example, one or more surfaces in a facility that processes substances consumed for their nutritive and/or recreational value (e.g., alcoholic beverages) can be treated by the methods described herein. It should be understood that any surface of a food processing facility that serves, or potentially could serve, as a point of contamination for the processing plant environment and/or food products can be treated by the methods described herein. For example, these surfaces include, but are not limited to, surfaces included in the plumbing system of a food processing facility (e.g., drain surfaces), surfaces of food processing equipment, and structural surfaces of a food processing facility.

In addition, it should be appreciated that compositions for, and methods of, treating a food product (e.g., a food product can be a substance consumed or eaten for its nutritive and/or recreational value) are provided. For example, a method of treating a food product of the present invention can include placing the food product in contact with one or more probiotic bacteria (e.g., competitive exclusion microorganisms) described herein. It should be understood that any portion of a food product that serves, or potentially could serve, as a point of contamination for the food product can be treated by the methods described herein.

The methods described herein inhibit the growth of undesirable microorganisms on such surfaces of food processing facilities and on food products. For example, inhibiting the growth of undesirable microorganisms (e.g., *L. monocytogenes*) includes, but is not limited to, the killing of, decreasing or stopping the growth of, exclusion of, or any other mechanism by which growth of undesirable microorganisms is controlled.

One illustrative method contemplated for treating a surface of a food processing facility or food product which has, or could have, a first population of microorganisms disposed thereon includes inoculating the surface with a composition that includes a second population of microorganisms. In one embodiment, the second population of microorganisms can be disposed in a biofilm. For example, an illustrative method includes disposing a biofilm containing a second population of microorganisms onto a surface, where the second population of microorganisms is inhibitory or bactericidal to the first population so that when the second population is placed in the presence of the first population the second populations inhibits the growth of the first population of microorganisms. Accordingly, it should be appreciated that a goal of the aforementioned inoculation is to contact a surface with a sufficient quantity of biofilm so that a second population of microorganisms contained in the biofilm can colonize the surface and inhibit the growth of a first population of microorganisms. It is also contemplated that, initially, the second population of microorganisms is not contained in a biofilm, but is capable of forming a biofilm after being placed on the surface. Therefore, this type of microorganism (i.e., the second population of microorganism) would initially not be contained in a biofilm when placed on the surface, but would thereafter form one to be contained in. It should be appreciated that having a probiotic microorganism, such as a competitive microorganism, in a biofilm facilitates the competitive microorganism's ability to inhibit the growth of undesirable microorganisms since the biofilm enables the competitive microorganism to adhere to surfaces for an extended period of time and not be washed away or significantly damaged by routine sanitation procedures. However, it should be appreciated that a biofilm is not absolutely required, and a goal of the aforementioned inoculation can be to contact a surface with a sufficient quantity of the second microorganism so that the second microorganism can colonize the surface and inhibit the growth of the first of microorganism in the absence of a biofilm. The above described methods and techniques discussed in reference to a surface in a food processing facility are also applicable to inhibiting the growth of undesirable microorganisms on the surfaces of food products.

As indicated above, a non-limiting example of a first population of microorganisms is one that includes *L. monocytogenes*, while examples of second populations of microorganisms include, but are not limited to, those competitive microorganisms discussed above which possess antagonistic activity to *L. monocytogenes*. In particular, with respect to controlling the growth of *L. monocytogenes*, the second population of microorganisms can include *Enterococcus durans* 141-1 having ATCC accession number PTA-4758, *Enterococcus durans* 152 having ATCC accession number PTA-4759, *Lactococcus lactis* C-1-92 having ATCC accession number PTA-4760, or *Lactococcus lactis* C-1-152 having ATCC accession number PTA-4761.

In addition to the subject matter discussed above, a kit for inhibiting the growth of or killing a first microorganism population disposed on a surface is contemplated. An illustrative example of such a kit can include a container containing a biofilm with a second microorganism population disposed in the biofilm. The second microorganism population is inhibitory to the first microorganism population so that when the surface is inoculated with the biofilm (i.e., the second microorganism population is placed in the presence of said first microorganism population) the second microorganism population inhibits the growth of the first population of microorganisms. In an alternative embodiment, the kit can include one container with a biofilm disposed therein and another container with the second microorganism population disposed therein. The second microorganism population can be mixed into the biofilm just prior to inoculating the surface, or the biofilm can be disposed onto the surface first, followed by the disposing of the second microorganism population into the biofilm. In another alternative, the kit can include, as discussed above, a second microorganism population capable of forming a biofilm after being disposed on the surface. Accordingly, this type of second microorganism population initially is not contained in a biofilm when place on the surface, but thereafter forms one to be contained in. As indicated above, a non-limiting example of a first population of microorganisms is one that includes *L. monocytogenes*, while examples of second populations of microorganisms which can be utilized in the kit include, but are not limited to, those competitive microorganisms discussed above which possess antagonistic activity to *L. monocytogenes*.

It should also be appreciated that the present disclosure also provides a method of selecting a population of inhibitory bacteria. An illustrative example of one such method includes (a) isolating naturally-occurring bacteria populations from a food processing facility, (b) culturing the isolated naturally-occurring bacteria populations; and (c) testing each isolated naturally-occurring bacteria population for the ability to inhibit the growth of a microorganism, where the isolated naturally-occurring bacteria populations having the ability to inhibit the growth of the microorganism are identified as a population of inhibitory bacteria. As indicated herein, one exemplary microorganism the aforementioned selecting method can be utilized for is *L. monocytogenes*.

While the invention has been illustrated and described in detail in the foregoing description, such an illustration and description is to be considered exemplary and not restrictive in character, it being understood that only the illustrative embodiments have been shown and described and that all changes and modifications within the spirit of the invention are desired to be protected.

There are a plurality of advantages of the present invention arising from the various features of the invention described herein. It will be noted that alternative embodiments of the present invention may not include all of the features described, but yet still benefit from at least some of the advantages of such features.

The invention claimed is:

1. A method of treating a surface of a food processing facility, to inhibit the growth of a first population of microorganisms comprising *Listeria monocytogenes* on said surface, said method comprising:

disposing an inhibitory composition, comprising a second population of microorganisms selected from the group consisting of *Enterococcus durans* having ATCC accession number PTA-4758, *Enterococcus durans* having ATCC accession number PTA-4759, *Lactococcus lactis* having ATCC accession number PTA-4760, and *Lactococcus lactis* having ATCC accession number PTA-4761, onto said surface of the food processing facility wherein the growth of said second population of microorganisms on said surface inhibits the growth of said first population of microorganisms.

2. The method of claim 1 wherein the treated surface is a floor drain.

3. The method of claim 1 wherein the temperature of said treated surface ranges from 3° C. to 29° C.

4. The method of claim 2 wherein the temperature of said floor drain ranges from 3° C. to 29° C.

5. The method of claim 1 wherein said inhibitory composition comprises two or more microorganisms selected from the group consisting of *Enterococcus durans* having ATCC accession number PTA-4758, *Enterococcus durans* having ATCC accession number PTA-4759, *Lactococcus lactis* having ATCC accession number PTA-4760, and *Lactococcus lactis* having ATCC accession number PTA-4761.

6. The method of claim 1 wherein said inhibitory composition comprises three or more microorganisms selected from the group consisting of *Enterococcus durans* having ATCC accession number PTA-4758, *Enterococcus durans* having ATCC accession number PTA-4759, *Lactococcus lactis* having ATCC accession number PTA-4760, and *Lactococcus lactis* having ATCC accession number PTA-4761.

7. The method of claim 1 wherein said inhibitory composition comprises a biofilm having disposed therein a microorganism selected from the group consisting of *Enterococcus durans* having ATCC accession number PTA-4758, *Enterococcus durans* having ATCC accession number PTA-4759, *Lactococcus lactis* having ATCC accession number PTA-4760, and *Lactococcus lactis* having ATCC accession number PTA-4761.

* * * * *

UNITED STATES PATENT AND TRADEMARK OFFICE
CERTIFICATE OF CORRECTION

PATENT NO. : 7,575,744 B2  Page 1 of 1
APPLICATION NO. : 10/535357
DATED : August 18, 2009
INVENTOR(S) : Doyle et al.

It is certified that error appears in the above-identified patent and that said Letters Patent is hereby corrected as shown below:

On the Title Page

Item [*] Notice: Subject to any disclaimer, the term of this patent is extended or adjusted under 35 U.S.C. 154(b) by 330 days.

Delete the phrase "by 330 days" and insert -- by 667 days --

Signed and Sealed this

Twenty-seventh Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,575,744 B2
APPLICATION NO. : 10/535357
DATED : August 18, 2009
INVENTOR(S) : Doyle et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1004 days.

Signed and Sealed this

Seventh Day of September, 2010

David J. Kappos
*Director of the United States Patent and Trademark Office*

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
cggctctgat taaattctga ag                                           22

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
cggttgagct ttaaatgaac                                              20
```

```
<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
agagaagtta tttacgatca ac                                              22

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
atctgacaac aaatcttttt gt                                              22
```